United States Patent
Wu

(10) Patent No.: US 9,192,531 B2
(45) Date of Patent: Nov. 24, 2015

(54) INTELLIGENT SENSING DEVICE WITH WARNING FUNCTION

(71) Applicant: Chuan-Shih Wu, Changhua (TW)

(72) Inventor: Chuan-Shih Wu, Changhua (TW)

( * ) Notice: Subject to any disclaimer, the term of this patent is extended or adjusted under 35 U.S.C. 154(b) by 97 days.

(21) Appl. No.: 14/091,462

(22) Filed: Nov. 27, 2013

(65) Prior Publication Data
US 2015/0145681 A1 May 28, 2015

(51) Int. Cl.
*G08B 23/00* (2006.01)
*A61G 7/00* (2006.01)

(52) U.S. Cl.
CPC ..................................... *A61G 7/001* (2013.01)

(58) Field of Classification Search
CPC ....................................................... G08B 21/22
USPC ...................................................... 340/573.1
See application file for complete search history.

(56) References Cited

U.S. PATENT DOCUMENTS

| | | | |
|---|---|---|---|
| 6,373,392 B1* | 4/2002 | Au | 340/573.1 |
| 7,652,581 B2* | 1/2010 | Gentry et al. | 340/573.1 |
| 2002/0070866 A1* | 6/2002 | Newham | 340/573.1 |
| 2012/0053424 A1* | 3/2012 | Kenalty et al. | 600/300 |

* cited by examiner

*Primary Examiner* — Kerri McNally
(74) *Attorney, Agent, or Firm* — Jackson IPG PLLC; Demian K. Jackson

(57) ABSTRACT

An intelligent sensing device with a warning function contains a flexible sensing pad, a signal processing device, a signal transmission device, a chargeable battery, and a signal receiving device. The flexible sensing pad senses a change of a connect signal by using a multi sensing mechanism. The signal processing device is electrically connected with the flexible sensing pad and processes a sensing signal transmitted by the flexible sensing pad. The signal transmission device is electrically coupled with the signal processing device and transmits a warning signal from the signal processing device. The chargeable battery supplies power to the signal processing device. When the power is less than a predetermined potential value, the signal processing device starts a low-level warning light or a low-level warning signal to indicate need to charge power. The signal receiving device receives the transmitted warning signal from the signal transmission device.

6 Claims, 9 Drawing Sheets

INTELLIGENT SENSING DEVICE WITH WARNING FUNCTION

FIELD OF THE INVENTION

The present invention relates to a sensing device, and more particularly to an intelligent sensing device with a warning function.

BACKGROUND OF THE INVENTION

Conventional sensing device contains a flexible circuit board or a pressure plate so as to sense a force change in a contact-sensing manner. However, such a conventional sensing device is produced at a high cost and has a poor reliability, a short service left and a lower sensing sensitivity. Also, the conventional sensing device cannot be used repeatedly.

Silver, graphite slurry and macromolecule resin are applied to manufacture a sensing device so as to conduct electricity efficiently. But the sensing device made of silver and graphite slurry is broken easily.

A conventional intelligent sensing device includes a flexible sensing film on which a sensing line set is arranged, and the sensing line set is made of a single material (such as silver or graphite) or two materials (silver and graphite slurry). As shown in FIG. 1, the flexible sensing film 100 has a single sensing line set 200.

Nevertheless, when single sliver or slurry graphite is used solely, ductility or surface hardness is quite low, thus breaking the sensing line set easily and transmitting signal wrongly.

The present invention has arisen to mitigate and/or obviate the afore-described disadvantages.

SUMMARY OF THE INVENTION

The primary object of the present invention is to provide an intelligent sensing device in which each sensing line set has a silver sensitive layer and a graphite-slurry sensing layer so as to increase flexibility and deformation and to lower oxidation rate, production cost and graphite impedance.

Another object of the present invention is to provide an intelligent sensing device which enhances healthcare safety.

To obtain the above objective, an intelligent sensing device provided by the present invention contains:

a flexible sensing pad provided to sense a change of a connect signal by ways of a multi sensing mechanism;

a signal processing device electrically connected with the flexible sensing pad and so as to process a sensing signal transmitted by the flexible sensing pad and then to illuminate a warning light or an emergency light, to transmit a warning signal or to execute face recognition and target search;

a signal transmission device electrically coupled with the signal processing device and transmitting a signal from the signal processing device in a wireless transmitting manner or a cable transmitting manner;

a chargeable battery provided to supply power to the signal processing device, wherein when the power is less than a predetermined potential value, the signal processing device starts a low-level warning light or a low-level warning signal, such that an intelligent sensing device is joined with an external power supply by the caregiver so as to charge power;

a signal receiving device served to receive a transmitted signal from the signal transmission device.

Preferably, the flexible sensing pad at least includes two flexible films and a flexible gap material, the two flexible films are formed on an upper surface and a lower surface of the flexible gap material, the flexible gap material includes a plurality of pores defined therein, two sensing line sets are arranged on two oppositely inner surfaces of the two flexible films, and each sensing line set has a silver sensitive layer and a graphite-slurry sensing layer which are stacked together, wherein the silver sensitive layer is defined between each flexible film and the graphite-slurry sensing layer; the two sensing line sets of the two flexible films electrically contact with each other via the plurality of pores after the two flexible films are pressed so as to form the multi-point sensing mechanisms, thus sensing a change of the contact signal.

Preferably, the flexible sensing pad further includes two covering layers covered on two outer surfaces of the two flexible films away from the flexible gap material.

It is preferable that the signal receiving device is a computer or a mobile device.

It is preferable that the flexible sensing pad is used as any one of a wheelchair cushion, a bed sensing pad, a ground sensing pad, and an anti-theft car mat.

Preferably, the signal processing device includes an alert module, an image module, and a monitoring module; the alert module is electrically connected with the image module and the monitoring module, and the alert module has an alert controlling circuit, a speaker circuit, a warning light control circuit, a low potential warning circuit, a reset circuit, and an emergency lighting circuit; the image module has a trigger control circuit, a face recognition circuit, and a tracking circuit; the alert controlling circuit is electrically coupled with the signal transmission device and is electrically in connection with the speaker circuit, the warning light control circuit, the low potential warning circuit, the reset circuit, and the emergency lighting circuit; and the trigger control circuit is electrically connected with the face recognition circuit and the tracking circuit.

DETAILED DESCRIPTION OF THE PREFERRED EMBODIMENTS

Figure 1:
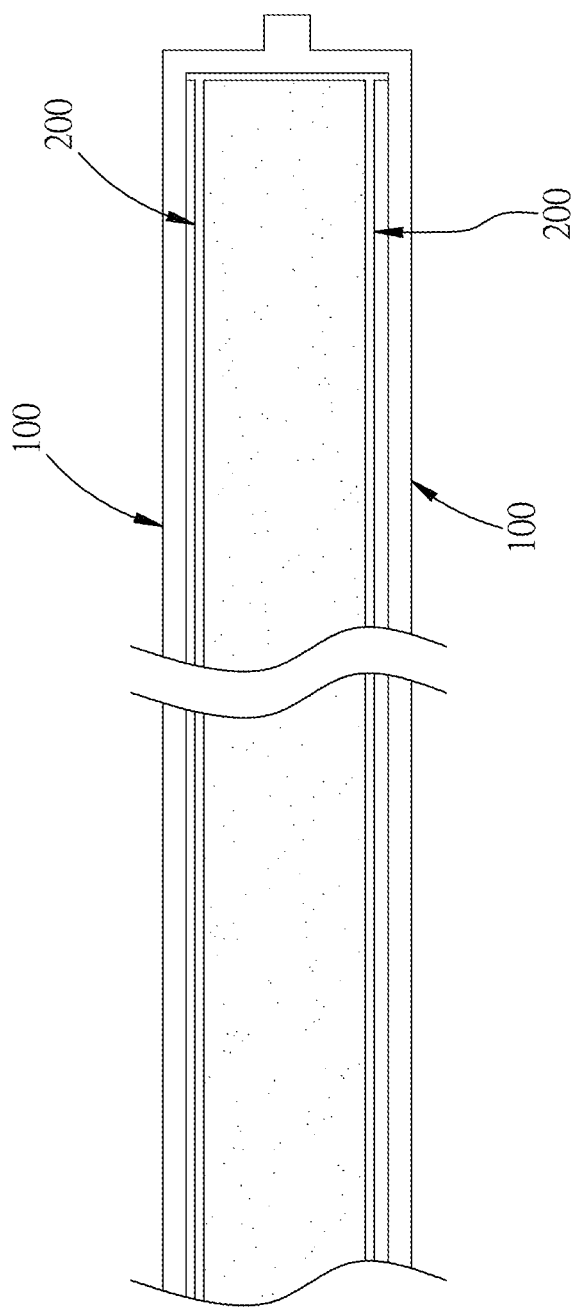
FIG. 1 is a cross sectional view of a conventional intelligent sensing device.
Figure 2:
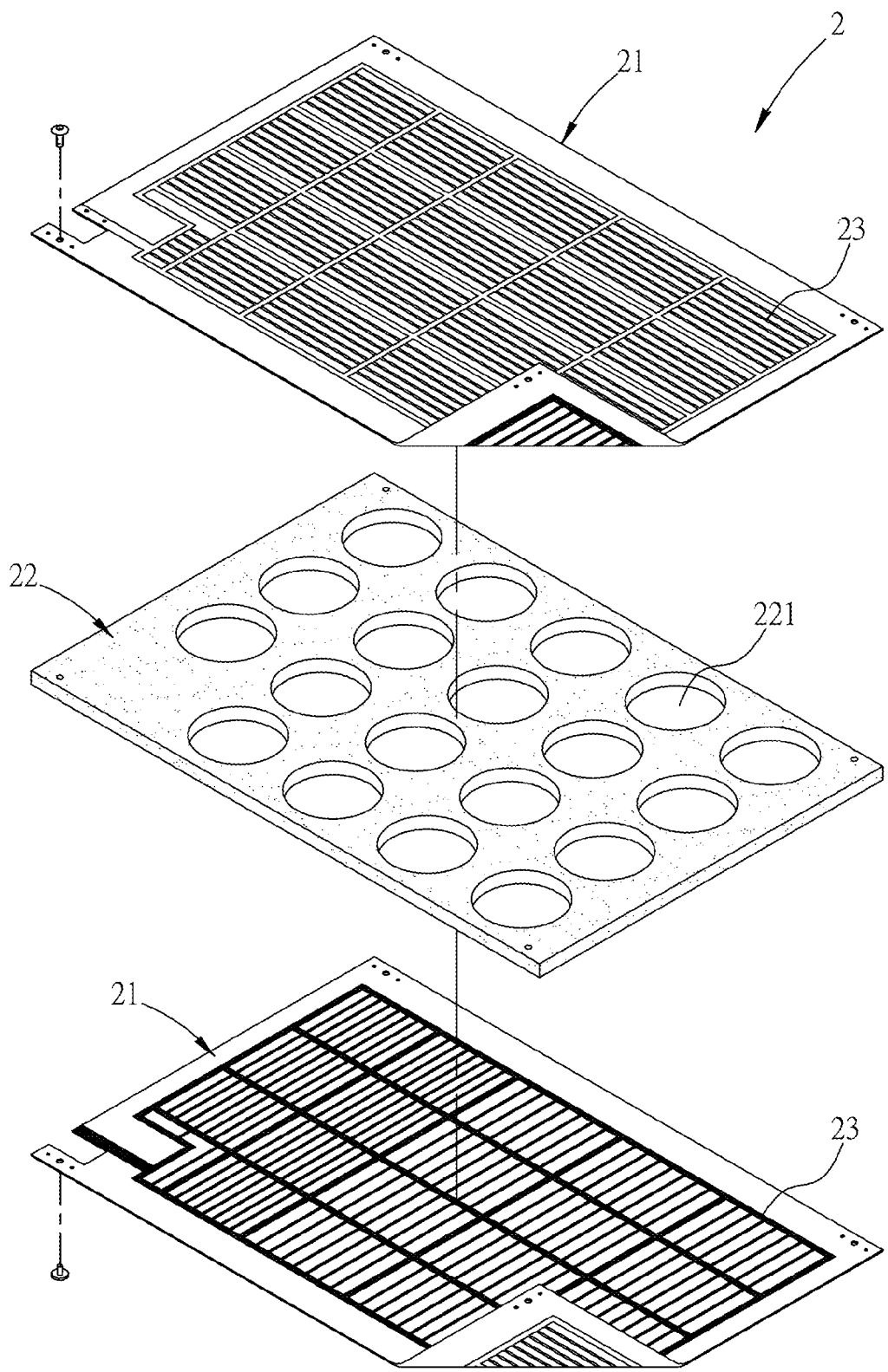
FIG. 2 is a perspective view showing the exploded components of an intelligent sensing device with a warning function according to a preferred embodiment of the present invention.
Figure 3:
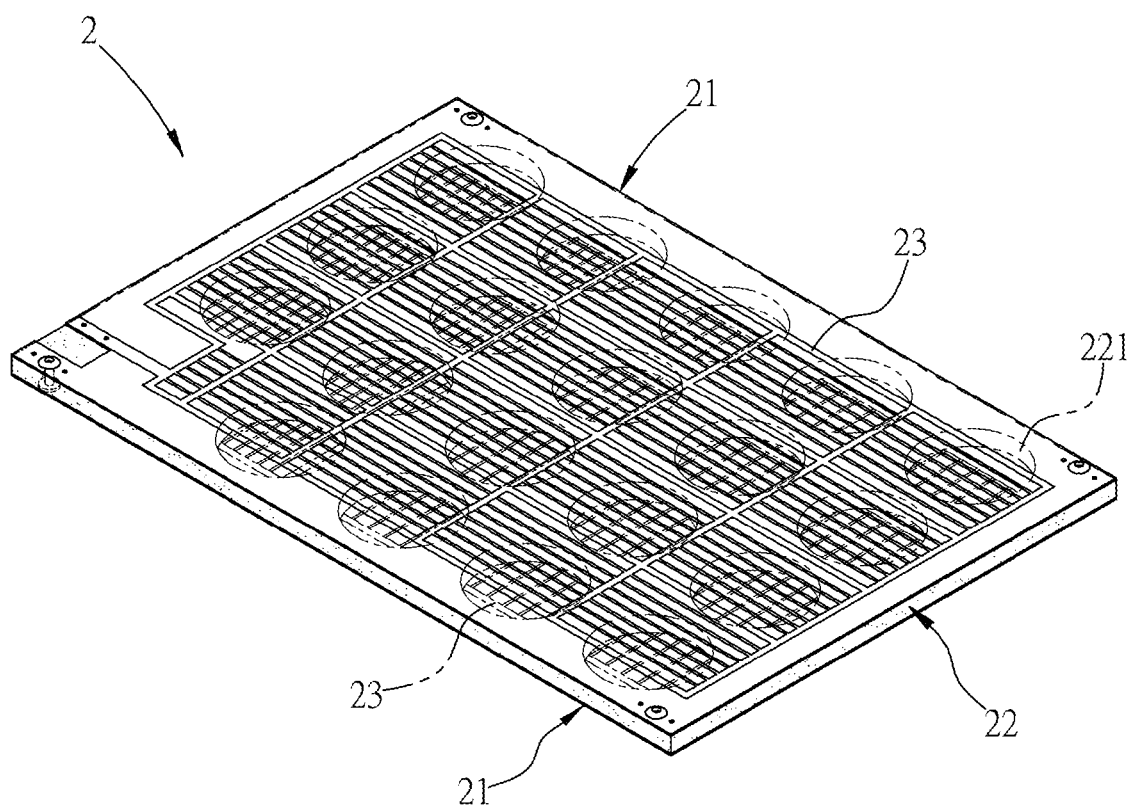
FIG. 3 is a cross sectional view showing a part of the intelligent sensing device with the warning function according to the preferred embodiment of the present invention.
Figure 4:
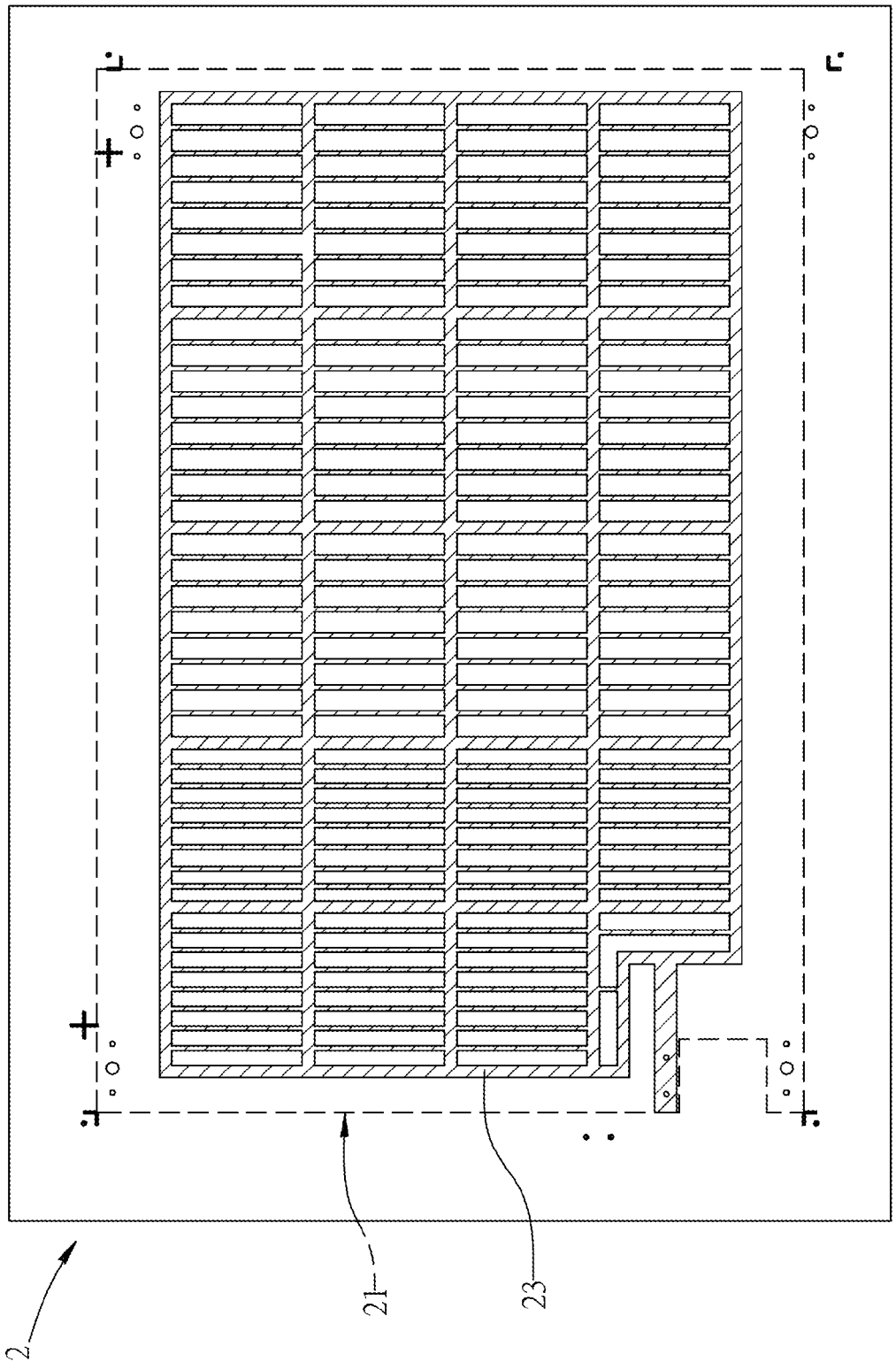
FIG. 4 is a cross sectional view showing the assembly of a lower flexible film of the intelligent sensing device with the warning function according to the preferred embodiment of the present invention.
Figure 5:
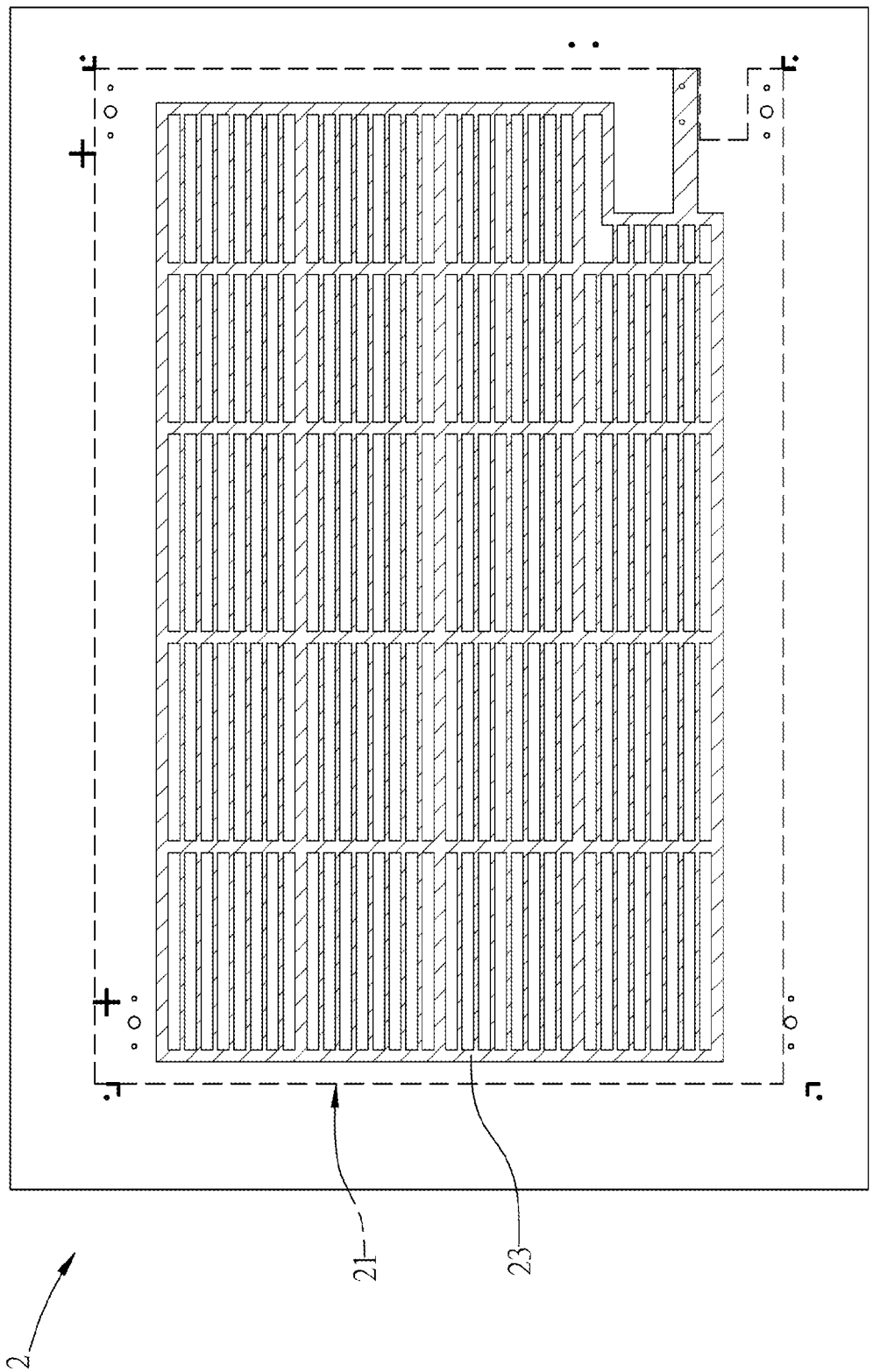
FIG. 5 is a cross sectional view showing the assembly of an upper flexible film of the intelligent sensing device with the warning function according to the preferred embodiment of the present invention.
Figure 6:
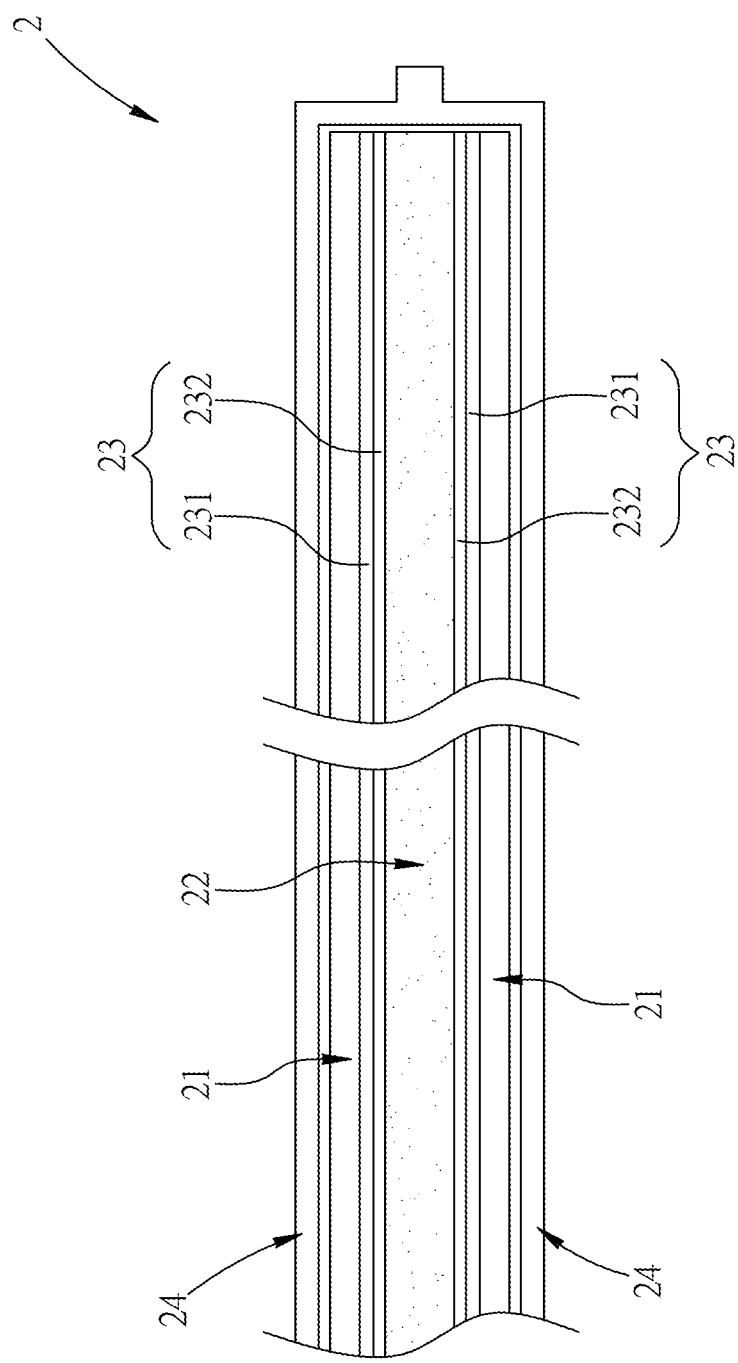
FIG. 6 is a cross sectional view showing the assembly of a flexible sensing cushion of the intelligent sensing device with the warning function according to the preferred embodiment of the present invention.

FIG. 2 is a perspective view showing the exploded components of an intelligent sensing device with a warning function according to a preferred embodiment of the present invention. FIG. 3 is a cross sectional view showing a part of the intelligent sensing device with the warning function according to the preferred embodiment of the present invention. FIG. 4 is a cross sectional view showing the assembly of a lower flexible film of the intelligent sensing device with the warning function according to the preferred embodiment of the present invention. FIG. 5 is a cross sectional view showing the assembly of an upper flexible film of the intelligent sensing device with the warning function according to the preferred embodiment of the present invention. FIG. 6 is a cross sectional view showing the assembly of a flexible sensing cushion of the intelligent sensing device with the warning function according to the preferred embodiment of the present invention.

With reference to FIGS. 2 to 6, an intelligent sensing device with a warning function according to a preferred embodiment of the present invention comprises a flexible sensing pad 2, a signal processing device 3, a signal transmission device 4, a rechargeable battery 5, and a signal receiving device 6.

The flexible sensing pad 2 senses a change of a contact signal by ways of a multi-point sensing mechanism. The flexible sensing pad 2 at least includes two flexible films 21 and a flexible gap material 22, the two flexible films 21 are made of PET plastic material and are formed on an upper surface and a lower surface of the flexible gap material 22. The flexible gap material 22 is a foam and includes a plurality of pores 211 defined therein, two sensing line sets 23 are arranged on two oppositely inner surfaces of the two flexible films 21, and each sensing line set 23 has a silver sensitive layer 231 and a graphite-slurry sensing layer 232 which are stacked together, wherein the silver sensitive layer 231 is defined between each flexible film 21 and the graphite-slurry sensing layer 232. Two sensing line sets 23 of the two flexible films 21 electrically contact with each other via the plurality of pores 221 after the two flexible films 21 are pressed so as to form the multi-point sensing mechanisms (i.e., a plural sensing units), thus sensing a change of the contact signal.

The flexible sensing pad 2 further includes two covering layers 24 covered on two outer surfaces of the two flexible films 21 away from the flexible gap material 22, wherein each covering layer 24 is made of TPU material.

The flexible sensing pad 2 is used as any one of a wheelchair cushion, a bed sensing pad, a ground sensing pad, and an anti-theft car mat.

Taking a wheelchair cushion for example, the flexible sensing pad 2 is placed on a wheelchair or a chair, and after medical/healthcare personnel starts the intelligent sensing device, a start signal is transmitted to a handheld communication system, a portable pager or a nurse call system of a nursing station via a cable/wireless transmission system or a network system so that a caregiver knows a patient's condition so as to prevent from a falling accident or a functional incontinence and to provide urgent assistance.

Taking the bed sensing pad for example, the flexible sensing pad 2 is placed on a bed or below a pillow, and after the medical/healthcare personnel starts the intelligent sensing device, the start signal is transmitted to the handheld communication system, the portable pager or the nurse call system of the nursing station via the cable/wireless transmission system or the network system so that the caregiver knows the patient's condition so as to prevent from the falling accident or the functional incontinence and to provide an urgent assistance. In addition, a preset time can be set in the intelligent sensing device so as to remind the caregiver to turn over a paralyzed patient after a reminder signal is transmitted to the handheld communication system, the portable pager or the nurse call system of the nursing station via the cable/wireless transmission system or the network system. Thereby, the paralyzed patient will not maintain the same posture which lying on the bed after a long period of time so as to avoid decubitus.

When the flexible sensing pad 2 is used as the ground sensing pad, it is put on a ground around the bed, and after the medical/healthcare personnel starts the intelligent sensing device, the start signal is transmitted to the handheld communication system, the portable pager or the nurse call system of the nursing station via the cable/wireless transmission system or the network system so that the caregiver knows the patient's condition so as to prevent from unexpected accident and to provide an urgent assistance.

When the flexible sensing pad 2 is served as the anti-theft car mat, it is fixed at a foot position of a car, so after a driver starts the intelligent sensing device and gets off the car, the start signal is transmitted to the handheld communication system or a central control system (such as a vehicle service center of a car dealer) via the wireless transmission system or the network system, thus obtaining anti-theft purpose.

Figure 9:
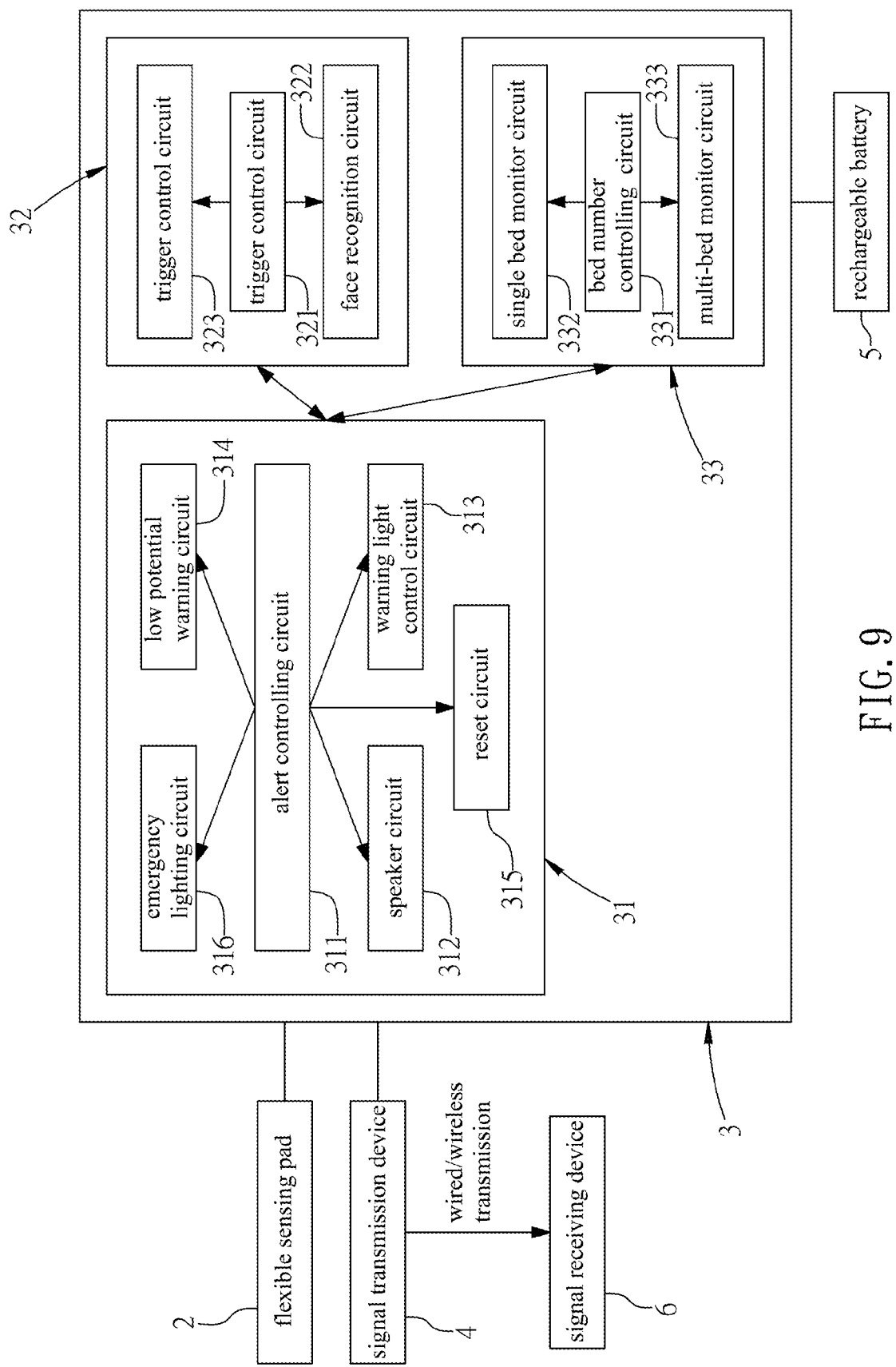
FIG. 9 is a diagram of a structure of the intelligent sensing device with the warning function according to the preferred embodiment of the present invention.

FIG. 9 is a diagram of a structure of the intelligent sensing device with the warning function according to the preferred embodiment of the present invention. As shown in FIG. 9, the signal processing device 3 is electrically connected with the flexible sensing pad 2 so as to process a sensing signal transmitted by the flexible sensing pad 2 and then to illuminate a warning light or an emergency light. In addition, the signal processing device 3 can transmit a warning signal or execute face recognition and target (i.e., the patient) search.

The signal processing device 3 includes an alert module 31, an image module 32, and a monitoring module 33. The alert module 31 is electrically connected with the image module 32 and the monitoring module 33. The alert module 31 has an alert controlling circuit 311, a speaker circuit 312, a warning light control circuit 313, a low potential warning circuit 314, a reset circuit 315, and an emergency lighting circuit 316. The image module 32 has a trigger control circuit 321, a face recognition circuit 322, and a tracking circuit 323. The alert controlling circuit 311 is electrically coupled with the signal transmission device 4 and is electrically in connection with the speaker circuit 312, the warning light control circuit 313, the low potential warning circuit 314, the reset circuit 315, and the emergency lighting circuit 316. The trigger control circuit 321 is electrically connected with the face recognition circuit 322 and the tracking circuit 323. The monitoring module 33 has a bed number controlling circuit 331, a single bed monitor circuit 332, and a multi-bed monitor circuit 333.

The signal transmission device 4 is electrically coupled with the signal processing device 3 and transmits a signal from the signal processing device 3 in a wireless transmitting manner or a cable transmitting manner. The chargeable battery 5 is provided to supply power to the signal processing device 3, and when the power is less than a predetermined potential value, the low potential warning circuit 314 starts a low-level warning light or a low-level warning signal through the speaker circuit 312 or the warning light control circuit 313, such that the intelligent sensing device is joined with an external power supply by the caregiver so as to charge power. The signal receiving device 6 is served to receive a transmitted signal from the signal transmission device 4 and is a computer or a mobile device.

Referring to FIG. 6, when a covering layer 24 contacts with the patient's skin, it absorbs a part of impact force from the patient so that the patient feels comfortably. The flexible gap material 22 is fixed between the two flexible films 21 and includes the plurality of pores 211 defined therein so as to absorb and spread the impact force, thus protecting the intelligent sensing device 2. Furthermore, the two covering layers 24 are applied to enhance comfort of the intelligent sensing device 2.

Figure 7:
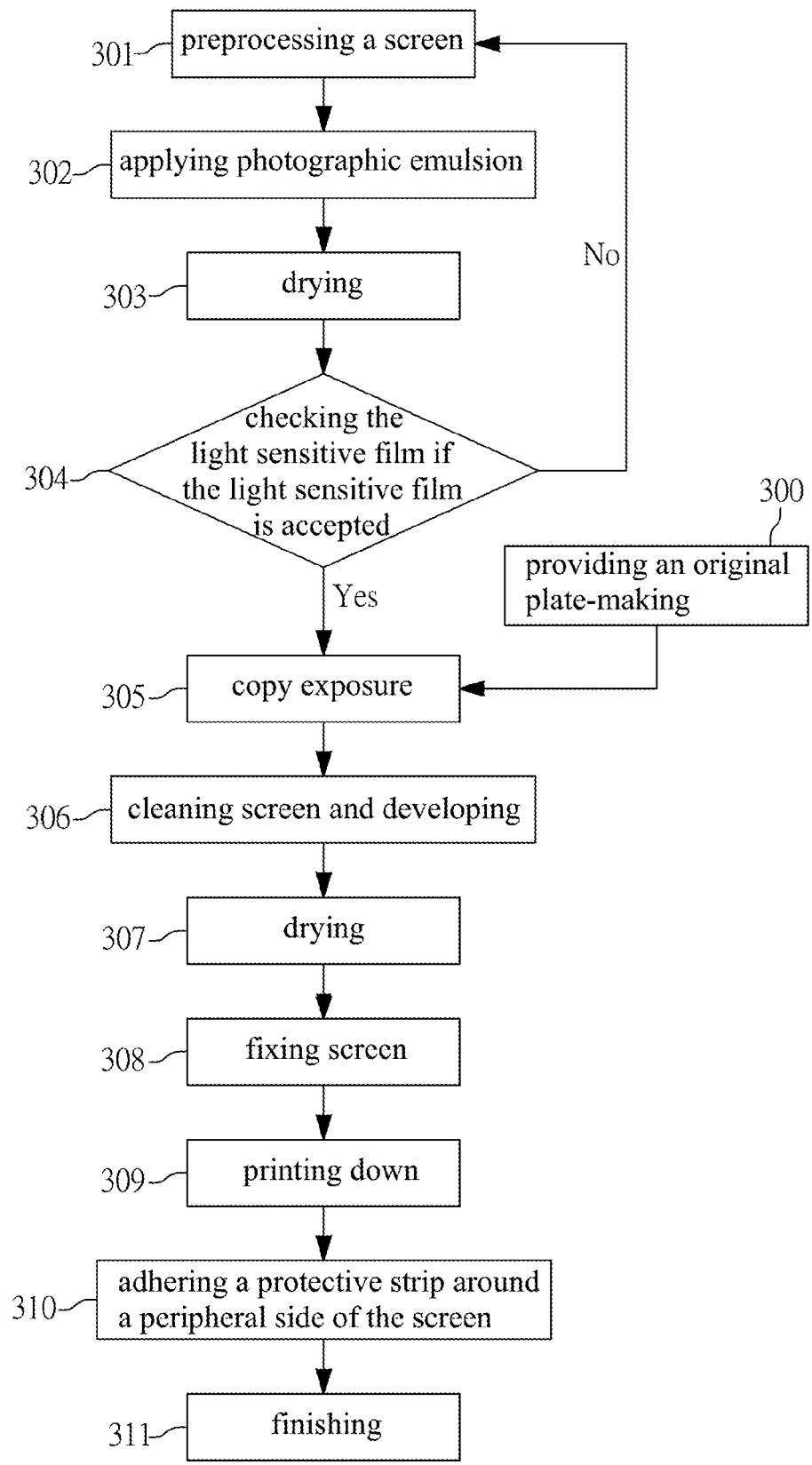
FIG. 7 is a flow chart of use steps of the intelligent sensing device according to the preferred embodiment of the present invention.

FIG. 7 is a flow chart showing stretching steps of a screen before manufacturing the intelligent sensing device.

Accordingly, the screen is stretched based on steps of:

301. preprocessing a screen including producing aluminum frame, putting the aluminum frame on the stretching machine, stretching the screen, and cleaning the screen;

302. applying photographic emulsion on a light sensitive film;

303. drying the screen;

304. placing the light sensitive film on a light sensing platform and checking the light sensitive film, wherein if the light sensitive film is defective, then going backing to a step 301; and if the light sensitive film is accepted, then going to next step;

305. executing a copy exposure, wherein an exposure time is set based on an applying quantity of the photographic emulsion;

306. soaking the screen in water for a period of time so as to clean the screen and display image;

307. drying the screen;

308. checking if the screen is defective, such as having break lines, forming in a gourd shape, having overlapped lines and uneven thickness, wherein if the screen is defective, then fixing the screen;

309. exposing the screen;

310. adhering a protective strip around a peripheral side of the screen;

311. finishing a stretching process of the screen.

Figure 8:
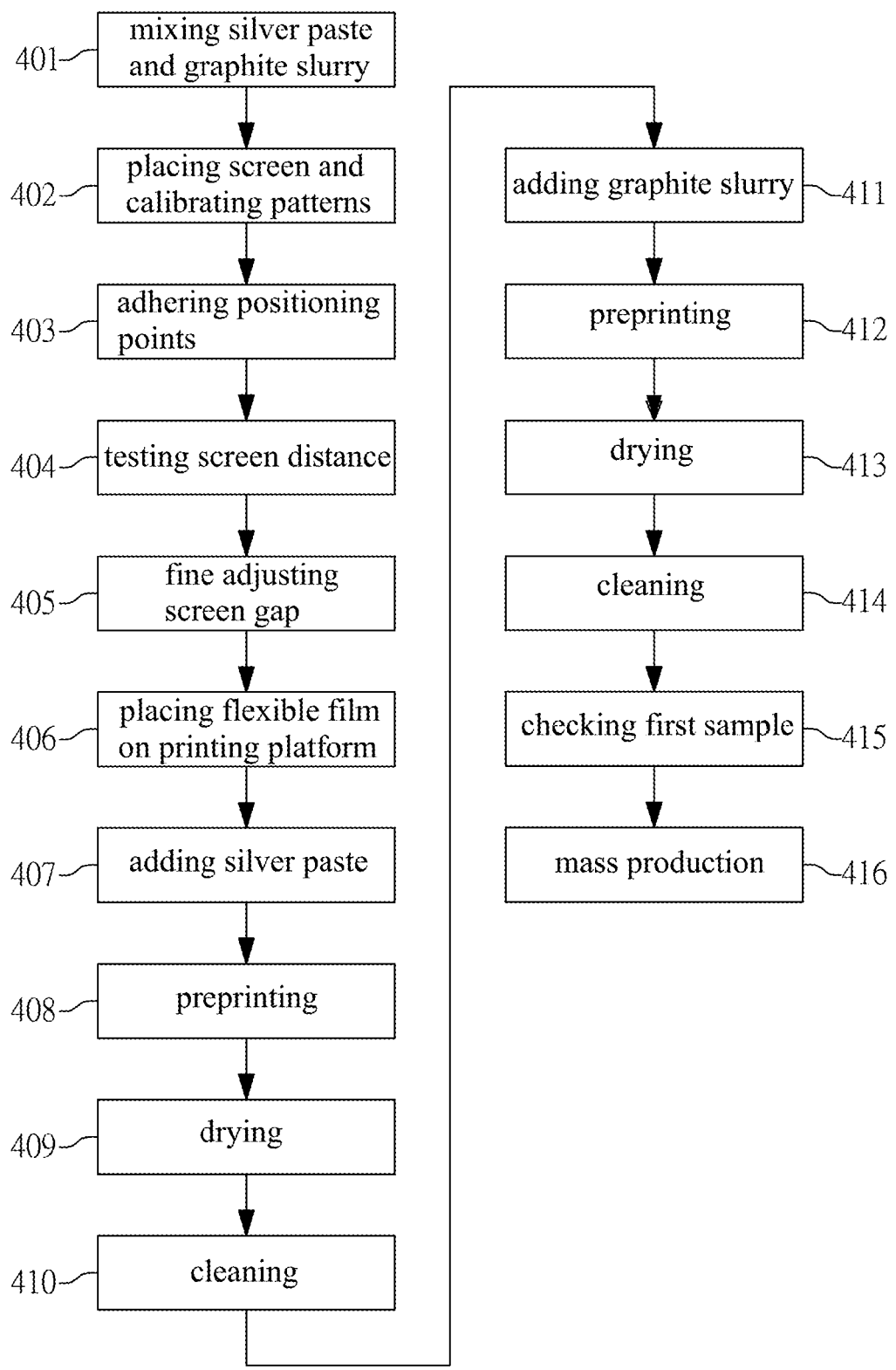
FIG. 8 is a flow chart of a screen printing process of the intelligent sensing device according to the preferred embodiment of the present invention.

FIG. 8 is a flow chart of a screen printing process of the intelligent sensing device according to the preferred embodiment of the present invention.

The screen printing process contains steps of:

401. mixing silver and graphite slurry according to a preset ratio;

402. placing a silk screen or a steel screen on a screen printing machine and calibrating patterns;

403. adhering positioning points;

404. testing a screen distance;

405. adjusting a screen gap;

406. placing each flexible film 21 on a printing platform;

407. adding silver;

408. executing preprinting process;

409. drying;

410. cleaning and aligning the screen printing machine, and adjusting a gap of the screen;

411. adding graphite slurry;

412. executing preprinting process;

413. drying;

414. cleaning;

415. forming a sensing line set 23 on the flexible film 21;

416. having a mass production.

It is to be noted that step 401 to step 406 are in a preprinting procedure, and step 407 to step 416 are in a printing procedure.

Thereby, the multi-point sensing mechanisms, an expandable buffer mechanism, a structure reinforcing mechanism, and a quick transmission mechanism are achieved. The multi-point sensing mechanisms and the expandable buffer mechanism can show a change between the pressing force and a resistance. The structure reinforcement mechanism is applied to prevent from a damage of the two sensing line sets. The quick transmission mechanism is used to conduct electric current quickly after the two sensing line sets are contacted so as to accelerate reaction and detection time of the signal processing device.

After the two sensing line sets 23 contact with each other, an internal resistance changes, and then a change signal is transmitted to the signal processing device 3 so as to start built-in functions.

To verify a method of manufacturing the intelligent sensing device, a reliability rest and simulate human actions can be realized. For instance, analyzing a change between the pressing force and the pressing force and the resistance at a sensing position in a single area (hereafter called unit); wherein the unit has to be repeatedly pressed or twisted up to $10^3$ to $10^4$ times. After monitoring the change and collecting changing data, the design value can be analyzed and adjusted so as to acquire optimal design parameters.

The multi-point sensing mechanisms can sense a change of the pressing force. In addition, an upper flexible film which is formed on an upper surface of the intelligent sensing device receives a maximum pressure and an instant impact force, and then the upper flexible film causes a deformation. The impact effect is acquired after timing 1.5 to 3 times of instant impact force, so a design difference, such as a deformation range or a resilient change of material, has to be considered.

When a chair cushion is made of the flexible sensing pad, and a weight of an upper body of the patient is 50 kg, it is assumed that a pressed area is 100 $cm^2$, a pressure of a unit area is F=500 N×100 $cm^2$=50 kPa. When the patient sits on the chair cushion, the impact force has to be a safety factor of above-mentioned pressing action. Accordingly, F=75 kPa to 150 kPa after 50 kPa times 1.5 to 3 times.

The expandable buffer mechanism and the multi-point sensing mechanisms can be analyzed by using finite element software to acquire a force mode, a stress distribution, and a large deformation to as to achieve optimization design.

During analyzing the intelligent sensing device by means of the finite element software, it is assumed that the intelligent sensing device receives 50 kPa of uniform force, and a pressure source contacts with the two sensing line sets, wherein a larger von Mises stress and nonlinear deformation act on the two sensing line sets 23 (i.e., sensing unit), such that the two sensing line sets 23 (i.e., sensing unit) cannot endure long-term pressuring force. Likewise, the expandable mechanism is a "sandwich" structure. Under the same action condition, the intelligent sensing device receives 50 kPa stress distribution, and the pressure source contacts with the two sensing line sets (i.e., sensing unit) directly, then the von Mises stress is absorbed by the flexible gap material 22 so as to completely absorb or decrease a force change on the two sensing line sets 23 (i.e., sensing unit), thereafter an excess force is spread to the plurality of pores 221, thereby protecting the flexible gap material 22.

The structure reinforcement mechanism is served in the screen printing process so to reinforce the graphite-slurry sensing layer 232, thus enhancing ductability and keeping surface hardness. Moreover, an excessive deformation of material molecules and grain sliding of graphite material are avoided. Preferably, each sensing line set has the silver sensitive layer and the graphite-slurry sensing layer so as to increase flexibility and deformation and to lower oxidation rate, production cost and graphite impedance.

In addition, the quick transmission mechanism can conduct free electrons via the silver sensitive layer 231 below the graphite-slurry sensing layer 232 quickly, thereby accelerating reaction and detection time.

While the preferred embodiments of the invention have been set forth for the purpose of disclosure, modifications of the disclosed embodiments of the invention as well as other embodiments thereof may occur to those skilled in the art. Accordingly, the appended claims are intended to cover all embodiments which do not depart from the spirit and scope of the invention.

What is claimed is:

1. An intelligent sensing device with a warning function comprising:
   a flexible sensing pad provided to sense a change of a connect signal by ways of a multi sensing mechanism;
   a signal processing device electrically connected with the flexible sensing pad and so as to process a sensing signal transmitted by the flexible sensing pad and then to perform one or more of illuminate a warning light or an emergency light, to transmit a warning signal, and to execute face recognition and target search;
   a signal transmission device electrically coupled with the signal processing device and transmitting the warning signal from the signal processing device in a wireless transmitting manner or a cable transmitting manner;
   a chargeable battery provided to supply power to the signal processing device, wherein when the power is less than a predetermined potential value, the signal processing device starts a low-level warning light or a low-level warning signal, such that the intelligent sensing device is joined with an external power supply by the caregiver so as to charge power;
   a signal receiving device served to receive the transmitted warning signal from the signal transmission device,
   wherein the flexible sensing pad at least includes two flexible films and a flexible gap material, the two flexible films are formed on an upper surface and a lower surface of the flexible gap material, the flexible gap material includes a plurality of pores defined therein, two sensing line sets are arranged on two oppositely inner surfaces of the two flexible films, and each sensing line has a silver sensitive layer and a graphite-slurry sensing layer which are stacked together, wherein the silver sensitive layer is defined between each flexible film and the graphite-slurry sensing layer; the two sensing line sets of the two flexible films electrically contact with each other via the plurality of pores after the two flexible films are pressed so as to form the multi-point sensing mechanism, thus sensing a change of the contact signal.

2. The intelligent sensing device with the warning function as claimed in claim 1, wherein the flexible sensing pad further includes two covering layers covered on two outer surfaces of the two flexible films away from the flexible gap material.

3. The intelligent sensing device with the warning function as claimed in claim 1, wherein the signal receiving device is a computer or a mobile device.

4. The intelligent sensing device with the warning function as claimed in claim 1, wherein the flexible sensing pad is used as any one of a wheelchair cushion, a bed sensing pad, a ground sensing pad, and an anti-theft car mat.

5. The intelligent sensing device with the warning function as claimed in claim 1, wherein the signal processing device includes an alert module, an image module, and a monitoring module; the alert module is electrically connected with the image module and the monitoring module, and the alert module has an alert controlling circuit, a speaker circuit, a warning light control circuit, a low potential warning circuit, a reset circuit, and an emergency lighting circuit; the image module has a trigger control circuit, a face recognition circuit, and a tracking circuit; the alert controlling circuit is electrically coupled with the signal transmission device and is electrically in connection with the speaker circuit, the warning light control circuit, the low potential warning circuit, the reset circuit, and the emergency lighting circuit; and the trigger control circuit is electrically connected with the face recognition circuit and the tracking circuit.

6. An intelligent sensing device with a warning function comprising:
   a flexible sensing pad provided to sense a change of a connect signal by ways of a multi sensing mechanism;
   a signal processing device electrically connected with the flexible sensing pad and so as to process a sensing signal transmitted by the flexible sensing pad and then to illuminate a warning light or an emergency light, to transmit a warning signal, and/or to execute face recognition and target search;
   a signal transmission device electrically coupled with the signal processing device and transmitting the warning signal from the signal processing device in a wireless transmitting manner or a cable transmitting manner;
   a chargeable battery provided to supply power to the signal processing device, wherein when the power is less than a predetermined potential value, the signal processing device starts a low-level warning light or a low-level warning signal, such that the intelligent sensing device is joined with an external power supply by the caregiver so as to charge power;
   a signal receiving device served to receive the transmitted warning signal from the signal transmission device,
   wherein the signal processing device includes an alert module, an image module, and a monitoring module; the alert module is electrically connected with the image module and the monitoring module, and the alert module has an alert controlling circuit, a speaker circuit, a warning light control circuit, a low potential warning circuit, a reset circuit, and an emergency lighting circuit; the image module has a trigger control circuit, a face recognition circuit, and a tracking circuit; the alert controlling circuit is electrically coupled with the signal transmission device and is electrically in connection with the speaker circuit, the warning light control circuit, the low potential warning circuit, the reset circuit, and the emergency lighting circuit; and the trigger control circuit is electrically connected with the face recognition circuit and the tracking circuit.

* * * * *